United States Patent [19]

Whitney

[11] Patent Number: 4,478,845

[45] Date of Patent: Oct. 23, 1984

[54] ANTIINFLAMMATORY AND/OR ANALGESIC IMIDAZOIMIDAZOLES

[75] Inventor: Joel G. Whitney, Kennett Square, Pa.

[73] Assignee: E. I. Du Pont de Nemours and Company, Wilmington, Del.

[21] Appl. No.: 459,189

[22] Filed: Jan. 19, 1983

[51] Int. Cl.$^3$ .................. A61K 31/415; A61K 31/44; C07D 487/04
[52] U.S. Cl. ................................ 424/273 R; 424/263; 546/256; 546/271; 548/324
[58] Field of Search ................ 548/324; 546/256, 271; 424/273 R, 263

[56] References Cited

U.S. PATENT DOCUMENTS 4,348,404  9/1982  Whitney .......................... 424/273 R

OTHER PUBLICATIONS

Elderfield, R. (Editor), *Heterocyclic Compounds*, vol. 5 John Wiley, New York, 1957, p. 239.
*Chemical Abstracts*, 91:57012p, (1979) [Giesecke, H., et al., Ger. Offen. 2,748,976, 5/3/79].
*Chemical Abstracts*, 73:25471z, (1970)[Kaufman, A., et al., Ger. Offen. 1,952,991, 5/6/70].

*Primary Examiner*—Richard A. Schwartz

[57] ABSTRACT

2,3-Diaryl-7,7-bis(fluorinated alkyl)imidazo[1,5-a]imidazoles, such as 2,3-bis(4-fluorophenyl)-5-methyl-7,7-bis(trifluoromethyl)imidazo[1,5-a]imidazole, are useful in the treatment of inflammation and/or pain.

6 Claims, No Drawings

ANTIINFLAMMATORY AND/OR ANALGESIC IMIDAZOIMIDAZOLES

BACKGROUND OF THE INVENTION

1. Field of Invention

This invention relates to imidazoimidazoles, their preparation, pharmaceutical compositions containing them and methods of using them to treat inflammation and/or pain in mammals. More particularly this invention relates to antiinflammatory and/or analgesic 2,3-diaryl-7,7-bis(fluorinated alkyl)imidazo[1,5-a]imidazoles.

2. Prior Art

U.S. Pat. No. 4,348,404, issued Sept. 7, 1982, to Joel G. Whitney describes 4,5-diaryl-α,α-bis(fluoroalkyl)-1H-imidazole-2-methanamines of the formula:

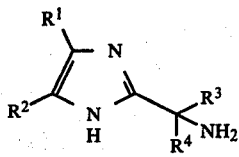

where $R^1$ and $R^2$ include pyridyl and substituted phenyl and, $R^3$ and $R^4$ independently include $CF_3$, $CF_2H$, and $CF_2CF_3$.

There is a continuing need for safe and effective antiinflammatory agents to treat inflammation, a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment as well.

The usefulness of many commercial antiinflammatories, however, is limited because of toxicity and adverse side-effects. Many produce gastric irritation and can cause changes in blood cells or can affect the central nervous system. Adreno-cortical steroids, for example, produce gastric irritation and suppression of normal adrenal function.

The present invention results from efforts to develop new anti-arthritic compounds with good antiinflammatory activity and minimal side effects that could be more effective in treating arthritis than are presently available drugs. In addition to antiinflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

According to the present invention there is provided a compound of the formula:

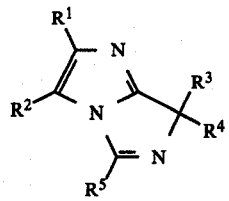

where $R^1$ and $R^2$ are independently pyridyl or

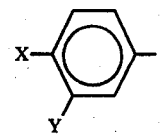

where X is H, F, Cl, Br, $R^6$, $OR^6$, $NR^6R^7$, $NO_2$ or $R^6S(O)_n$ where n is 0, 1, 2

Y is H, F or Cl; provided that when Y is F or Cl then X must be F or Cl;

$R^3$ and $R^4$ are independently $CF_3$, $CF_2H$, $CF_2Cl$, $CFCl_2$, or $CF_2CF_3$, provided that no more than one of $R^3$ and $R^4$ is $CF_2CF_3$, and $R^5$, $R^6$ and $R^7$ are independently $CH_3$ or $C_2H_5$; or a pharmaceutically suitable salt thereof.

There is also provided a process for preparing the aforesaid compounds which comprises contacting a methanamine of the formula:

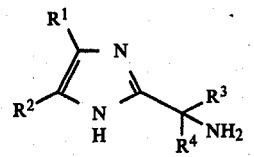

where $R^1$, $R^2$, $R^3$ and $R^4$ are as defined above with an anhydride of the formula $(R^5CO)_2O$ or an acid chloride of the formula $R^5COCl$ where $R^5$ is $CH_3$ or $C_2H_5$.

Also provided are pharmaceutical compositions containing at least one of the aforesaid compounds and methods of using them to treat inflammation and/or pain in mammals.

Preferred Scope

Compounds of preferred scope are those of formula I where $R^1$ and $R^2$ are independently

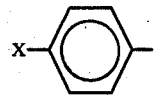

where X is F, $OR^6$ or $R^6$ where $R^6$ is as defined.

More preferred are compounds of preferred scope where $R^3$ and $R^4$ are $CF_3$; and $R^5$ and $R^6$ are $CH_3$.

Specifically preferred is 2,3-bis(4-fluorophenyl)-5-methyl-7,7-bis(trifluoromethyl)imidazo[1,5-a]imidazole having the formula:

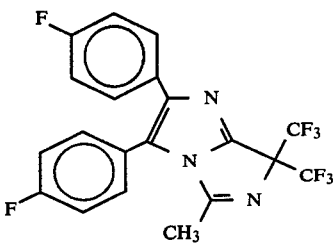

Pharmaceutical Salts

Pharmaceutically suitable salts and their preparation are well known to those skilled in pharmaceuticals and can be used in the present invention. They include salts formed with mineral acids such as hydrochloric, nitric, and sulfuric acid.

Synthesis

The compounds of this invention, I, can be prepared by treating a 4,5-diaryl-$\alpha,\alpha$-bis(fluoroalkyl)-1H-imidazole-2-methanamine of formula II with an acid anhydride, $(R^5CO)_2O$, or an acid chloride, $R^5COCl$, where $R^1$, $R^2$, $R^3$, $R^4$ and $R^5$ are as defined above.

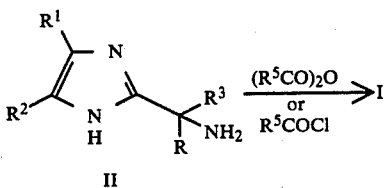

Compounds of formula II and their preparation are described in U.S. Pat. No. 4,348,404 to Joel G. Whitney, issued Sept. 7, 1982.

The reaction may be carried out in the absence of added solvent, or, optionally, in the presence of an inert solvent such as a hydrocarbon (toluene) or chlorinated hydrocarbon (chloroform). Reaction temperatures from room temperature to the boiling point of the acid anhydride or acid chloride reactant or of the solvent may be used; temperatures of 120°–170° C. are preferred.

When the aryl groups $R^1$ and $R^2$ are not the same, a mixture of isomeric imidazoimidazoles may be obtained, both of which are compounds of this invention. Their separation can be achieved by use of crystallization, chromatographic techniques, or other techniques well known to those skilled in the art.

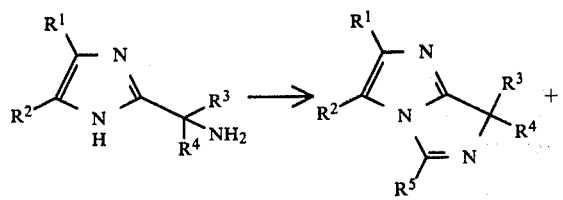

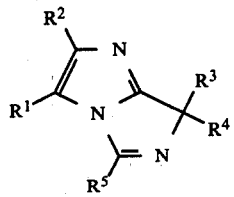

In cases where $R^3$ and $R^4$ are not the same, and/or where at least one of $R^1$ and $R^2$ is 4-alkylsulfinylphenyl, the compounds of this invention exist as mixtures of enantiomers or diastereoisomers, which may be separated by conventional techniques. Both the mixtures and preparations enriched in one or more of the constituent isomers are included in this invention.

EXAMPLE 1

Preparation of 2,3-bis(4-Fluorophenyl)-5-methyl-7,7-bis(trifluoromethyl)imidazo[1,5-a]imidazole (I; $R^1=R^2=4-FC_6H_4$, $R^3=R^4=CF_3$, $R^5=CH_3$)

A mixture of 3.0 g of 4,5-bis(4-fluorophenyl)-$\alpha,\alpha$-bis(trifluoromethyl)-1H-imidazole-2-methanamine and acetic anhydride (20 ml) was heated at reflux for about 40 hours, at which time the methanamine starting material was all consumed as indicated by thin layer chromatography. The cooled mixture was evaporated in vacuo and treated with xylene and re-evaporated twice. Crystallization of the residue (3.36 g) from 1-chlorobutane provided 0.81 g of a white powder, m.p. 203°–205° C. The residue from the mother liquor was chromatographed (dry $SiO_2$ column, 4:1 hexane/ethyl acetate) to provide the title compound, 1.85 g, m.p. 151°–153° C.

Microanalysis was performed on a sample prepared essentially as described above, m.p. 152°–154° C. Calc. for $C_{20}H_{11}F_8N_3$: C, 53.9; H, 2.4; N, 9.4. Found: C, 54.0; H, 2.5; N, 9.4.

EXAMPLE 2

Preparation of 2,3-bis(4-Methoxyphenyl)-5-methyl-7,7-bis(trifluoromethyl)imidazo[1,5-a]imidazole (I; $R^1=R^2=4-CH_3OC_6H_4$, $R^3=R^4=CF_3$, $R^5=CH_3$)

Following the procedure of Example 1, but substituting 4,5-bis(4-methoxyphenyl)-$\alpha,\alpha$-bis(trifluoromethyl)-1H-imidazole-2-methanamine as the substrate, the title compound was obtained, m.p. 160°–163° C.

EXAMPLE 3

Preparation of 2,3-bis(4-Methylphenyl)-5-methyl-7,7-bis(trifluoromethyl)imidazo[1,5-a]imidazole (I; $R^1=R^2=4-CH_3C_6H_4$, $R^3=R^4=CF_3$, $R^5=CH_3$)

Following the procedure of Example 1, but substituting 4,5-bis(4-methylphenyl)-$\alpha,\alpha$-bis(trifluoromethyl)-1H-imidazole-2-methanamine as the substrate, the title compound was obtained, m.p. 179°–181° C.

In Table I are listed the compounds prepared in Examples 1–3 and other imidazoimidazoles of the invention which may be prepared by the procedure of Example 1.

TABLE I

| Ex. No. | $R^1$ | $R^2$ | $R^3$ | $R^4$ | $R^5$ | m.p. (°C.) |
|---|---|---|---|---|---|---|
| 1 | 4-FC$_6$H$_4$ | 4-FC$_6$H$_4$ | CF$_3$ | CF$_3$ | CH$_3$ | 151–153° |
| 2 | 4-CH$_3$OC$_6$H$_4$ | 4-CH$_3$OC$_6$H$_4$ | CF$_3$ | CF$_3$ | CH$_3$ | 160–163° |
| 3 | 4-CH$_3$C$_6$H$_4$ | 4-CH$_3$C$_6$H$_4$ | CF$_3$ | CF$_3$ | CH$_3$ | 179–181° |
| 4 | 4-BrC$_6$H$_4$ | 4-BrC$_6$H$_4$ | CF$_3$ | CF$_3$ | CH$_3$ | |
| 5 | C$_6$H$_5$ | C$_6$H$_5$ | CF$_3$ | CF$_3$ | CH$_3$ | |
| 6 | 4-(CH$_3$)$_2$NC$_6$H$_4$ | 4-(CH$_3$)$_2$NC$_6$H$_4$ | CF$_3$ | CF$_3$ | CH$_3$ | |
| 7 | 4-FC$_6$H$_4$ | 4-NO$_2$C$_6$H$_4$ | CF$_3$ | CF$_3$ | CH$_3$ | |
| 8 | 4-FC$_6$H$_4$ | 4-CH$_3$SC$_6$H$_4$ | CF$_3$ | CF$_3$ | CH$_3$ | |
| 9 | 4-FC$_6$H$_4$ | 3-pyridyl | CF$_3$ | CF$_3$ | CH$_3$ | |
| 10 | 4-FC$_6$H$_4$ | 4-FC$_6$H$_4$ | CF$_3$ | CF$_3$ | C$_2$H$_5$ | |
| 11 | 4-FC$_6$H$_4$ | 4-FC$_6$H$_4$ | CF$_3$ | CF$_2$H | CH$_3$ | |
| 12 | 4-FC$_6$H$_4$ | 4-FC$_6$H$_4$ | CFCl$_2$ | CF$_2$Cl | CH$_3$ | |
| 13 | 4-FC$_6$H$_4$ | 4-FC$_6$H$_4$ | CF$_3$ | CF$_2$CF$_3$ | CH$_3$ | |
| 14 | 4-FC$_6$H$_4$ | 4-CH$_3$SO$_2$C$_6$H$_4$ | CF$_3$ | CF$_3$ | CH$_3$ | |
| 15 | 4-ClC$_6$H$_4$ | 4-C$_2$H$_5$OC$_6$H$_4$ | CF$_3$ | CF$_3$ | CH$_3$ | |
| 16 | 4-FC$_6$H$_4$ | 4-C$_2$H$_5$SO$_2$C$_6$H$_4$ | CF$_3$ | CF$_3$ | CH$_3$ | |
| 17 | 4-FC$_6$H$_4$ | 4-C$_2$H$_5$C$_6$H$_4$ | CF$_3$ | CF$_3$ | CH$_3$ | |
| 18 | 4-FC$_6$H$_4$ | 3,4-Cl$_2$C$_6$H$_3$ | CF$_3$ | CF$_3$ | CH$_3$ | |
| 19 | 4-FC$_6$H$_4$ | 4-CH$_3$SOC$_6$H$_4$ | CF$_3$ | CF$_3$ | CH$_3$ | |
| 20 | 4-FC$_6$H$_4$ | 4-(C$_2$H$_5$)$_2$NC$_6$H$_4$ | CF$_3$ | CF$_3$ | CH$_3$ | |

Dosage Forms

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Some of the compounds of this invention form salts. Solutions for parenteral administration of these compounds contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 75 milligrams of the active ingredient. The capsules are washed and dried.

Tablets

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

Use

To detect and compare the antiinflammatory activities of compounds in this series and standard drugs, a test was used based on a standard model of arthritis for which there is good correlation with human efficacy. The model is adjuvant-induced arthritis in rats. Federation Proceedings, Vol. 32, No. 2, 1973 "Models Used for the Study and Therapy of Rheumatoid Arthritis'-'—Symposium of the American Society for Pharmacology and Experimental Therapeutics—states "The rat polyarthritis produced by intradermal injection of a suspension of Mycobacterium tuberculosis in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized Mycobacterium butyricum suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control} \quad \text{Treatment Group}}{\text{Mean Paw Volume (ml)} - \text{Mean Paw Volume (ml)}} \times 100 =$$
$$\overline{\text{Arthritic Control} \quad \text{Non-Arthritic Control}}$$
$$\text{Mean Paw Volume (ml)} - \text{Mean Paw Volume (ml)}$$

% Decrease from Control Mean Paw Volume.

Dose-response regression lines of the percent decrease are plotted on semi-log paper by visual fit and the ED50% decrease from control paw volume is determined by inspection. Data for some of the compounds of this invention are summarized in Table II.

Compounds from this series were also compared to indomethacin, phenylbutazone, ibuprofen, and aspirin.

Phenylquinone Writhing Test

A standard procedure for detecting and comparing the analgesic activity of compounds in this series for which there is a good correlation with human efficacy is the standard phenylquinone writhing test modified from Siegmund, et al., Proc. Soc. Exp. Biol. Med., 95, 729 (1957). A test compound suspended in 1% methylcellulose was given orally to fasted (17–21 hours) female white mice, 5–20 animals per double blind test. Aqueous (0.01% phenyl-p-benzoquinone) phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., Bact. Rev., 11, 115–145 (1947); the time of peak activity was determined for many of the compounds. Data for some of the compounds are summarized in Table II together with data for some standard analgetic-antiinflammatory drugs.

TABLE II

| | Biological Activity | |
|---|---|---|
| Example | Adjuvant Arthritic $ED_{50}$ (mg/kg) | Phenylquinone Writhing (PQW) $ED_{50}$ (mg/kg) |
| 1 | 6.5 | 135 |
| 2 | (31% at 45)[1] | 21 |
| 3 | (44% at 45)[1] | >108 |
| Indomethacin | 0.3 | 0.35 |
| Phenylbutazone | 10 | 80 |
| Ibuprofen | 100 | 10 |
| Aspirin | 305 | 135 |

[1]Values in parentheses indicate the percent reduction in paw volume at the indicated dose.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound having the formula:

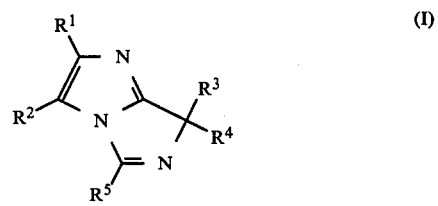

(I)

where $R^1$ and $R^2$ are independently pyridyl or

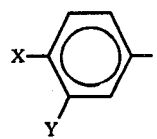

where X is H, F, Cl, Br, $R^6$, $OR^6$, $NR^6R^7$, $NO_2$ or $R^6S(O)_n$ where n is 0, 1, 2

Y is H, F, or Cl; provided that when y is F or Cl then X must be F or Cl;

$R^3$ and $R^4$ are independently $CF_3$, $CF_2H$, $CF_2Cl$, $CFCl_2$, or $CF_2CF_3$, provided that no more than one of $R^3$ and $R^4$ is $CF_2CF_3$, and $R^5$, $R^6$ and $R^7$ are independently $CH_3$ or $C_2H_5$;

or a pharmaceutically suitable salt thereof.

2. A compound of claim 1 wherein $R^1$ and $R^2$ are independently

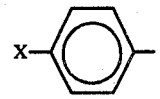

where X is F, $OR^6$ or $R^6$.

3. A compound of claim 2 wherein $R^3$ and $R^4$ are $CF_3$, and $R^5$ and $R^6$ are $CH_3$.

4. The compound of claim 1 which is 2,3-bis(4-fluorophenyl)-5-methyl-7,7-bis(trifluoromethyl)imidazo[1,5-a]imidazole.

5. A pharmaceutical composition consisting essentially of a suitable pharmaceutical carrier and an effective antiinflammatory or analgesic amount of at least one compound of claim 1, claim 2, claim 3 or claim 4.

6. A method of treating inflammation, pain or both in a mammal which comprises administering to the mammal an effective antiinflammatory or analgesic amount of at least one compound of claim 1, claim 2, claim 3 or claim 4.

* * * * *